(12) United States Patent
Ship et al.

(10) Patent No.: US 12,383,704 B2
(45) Date of Patent: Aug. 12, 2025

(54) VARIABLE-STIFFNESS DISTAL EXTENSION FOR A BLOOD PUMP SYSTEM

(71) Applicant: ABIOMED, Inc., Danvers, MA (US)

(72) Inventors: Alexander Ship, Danvers, MA (US); Zhenghong Tao, Winchester, MA (US)

(73) Assignee: ABIOMED, Inc., Danvers, MA (US)

( * ) Notice: Subject to any disclaimer, the term of this patent is extended or adjusted under 35 U.S.C. 154(b) by 427 days.

(21) Appl. No.: 16/851,920

(22) Filed: Apr. 17, 2020

(65) Prior Publication Data

US 2020/0330664 A1    Oct. 22, 2020

Related U.S. Application Data

(60) Provisional application No. 62/835,636, filed on Apr. 18, 2019.

(51) Int. Cl.
 *A61M 60/135*    (2021.01)
 *A61M 25/00*    (2006.01)
 (Continued)

(52) U.S. Cl.
 CPC .... *A61M 25/0102* (2013.01); *A61M 25/0043* (2013.01); *A61M 25/09* (2013.01);
 (Continued)

(58) Field of Classification Search
 CPC .. A61M 60/857; A61M 60/845; A61M 60/00; A61M 60/80; A61M 69/859;
 (Continued)

(56) References Cited

U.S. PATENT DOCUMENTS 6,637,435 B2 * 10/2003 Ciaglia ............. A61M 16/0472
                                              128/207.29
6,743,227 B2    6/2004 Seraj et al.
(Continued)

FOREIGN PATENT DOCUMENTS

CN         1208369 A     2/1999
CN       105193533 A    12/2015
(Continued)

OTHER PUBLICATIONS

International Search Report and Written Opinion for Application No. PCT/US20/28751 dated Aug. 24, 2020.
(Continued)

*Primary Examiner* — Tan-Uyen T Ho
*Assistant Examiner* — Bridget E. Rabaglia
(74) *Attorney, Agent, or Firm* — Botos Churchill IP Law LLP (57) ABSTRACT

Systems and methods for providing a blood pump system having a variable stiffness distal extension are disclosed. A variable stiffness distal extension may have at least one section of continuously varying stiffness, resulting in a stiffness profile that decreases in a distal direction along a length of the distal extension. The varying stiffness may be accomplished by varying one or more radial dimensions of the extension. For example, in some implementations, an outer diameter of a distal extension may decrease along at least a portion of a distal extension. The distal extension may include a lumen configured to receive a longitudinally extending element.

32 Claims, 3 Drawing Sheets

(51) Int. Cl.
  *A61M 25/01* (2006.01)
  *A61M 25/09* (2006.01)
  *A61M 60/13* (2021.01)
  *A61M 60/174* (2021.01)
  *A61M 60/857* (2021.01)
  *A61M 60/865* (2021.01)

(52) U.S. Cl.
  CPC .......... *A61M 60/13* (2021.01); *A61M 60/135* (2021.01); *A61M 60/174* (2021.01); *A61M 60/857* (2021.01); *A61M 60/865* (2021.01); *A61M 25/0023* (2013.01); *A61M 2025/0063* (2013.01); *A61M 2025/09133* (2013.01); *A61M 2025/0915* (2013.01)

(58) Field of Classification Search
  CPC ........ A61M 60/122; A61M 2025/0915; A61M 2025/0068; A61M 2025/0063; A61M 25/0043; A61M 25/0102; A61M 25/09; A61M 25/0023; A61M 60/135; A61M 2025/09133; A61M 25/0133; A61M 25/0161; A61M 39/00; A61M 15/0136; A61M 25/0138; A61M 25/0144; A61M 2025/0161; A61M 25/0041; A61M 60/216; A61M 25/0068; A61M 2025/0681; A61M 25/0662; A61M 25/01; A61M 25/00; A61B 17/32; A61B 17/32053; A61B 17/3207; A61B 2017/22094; A61B 2017/003; A61B 2017/00305; A61B 18/1492; A61B 2017/00243; A61B 2090/3966; A61B 6/12; A61B 2018/00577; A61B 34/20; A61B 8/12; A61B 2017/00247; A61B 2018/00351; A61B 2017/1205; A61B 17/00234; A61B 5/0215; A61B 17/12122; A61B 17/3415; A61B 17/12172; A61B 5/6852; A61B 5/15003
  See application file for complete search history.

(56) References Cited

U.S. PATENT DOCUMENTS

| | | | |
|---|---|---|---|
| 7,037,290 B2 | 5/2006 | Gardeski et al. | |
| 7,717,899 B2 | 5/2010 | Bowe et al. | |
| 7,766,868 B2 | 8/2010 | Goode et al. | |
| 7,914,436 B1* | 3/2011 | Kung | A61M 60/515 600/18 |
| 9,814,814 B2 | 11/2017 | Corbett et al. | |
| 2005/0203425 A1* | 9/2005 | Langston | A61B 5/02158 264/155 |
| 2006/0074398 A1* | 4/2006 | Whiting | A61M 25/0662 604/510 |
| 2006/0271085 A1 | 11/2006 | Siess | |
| 2009/0105652 A1* | 4/2009 | Beal | A61B 17/3421 604/170.03 |
| 2012/0172655 A1* | 7/2012 | Campbell | A61M 60/13 600/16 |
| 2015/0283357 A1 | 10/2015 | Lampropoulos et al. | |
| 2015/0328382 A1* | 11/2015 | Corbett | A61M 60/865 600/16 |
| 2016/0106323 A1 | 4/2016 | Ou et al. | |
| 2017/0232169 A1 | 8/2017 | Muller | |
| 2023/0099453 A1 | 3/2023 | Siess | |

FOREIGN PATENT DOCUMENTS

| | | |
|---|---|---|
| CN | 106166323 A | 11/2016 |
| JP | 2007501644 A | 2/2007 |
| JP | 2017515587 A | 6/2017 |
| JP | 2018502673 A | 2/2018 |
| WO | 9725190 A1 | 7/1997 |
| WO | 2015175711 A1 | 11/2015 |
| WO | 2016065278 A1 | 4/2016 |
| WO | 2018089970 A1 | 5/2018 |
| WO | 2019038343 A1 | 2/2019 |

OTHER PUBLICATIONS

Partial Search Report and Provisional Opinion for Application No. PCT/US2020/028751 dated Jul. 3, 2020.
Office Action from corresponding Chinese Patent Application No. 202080040492.0 dated Jun. 13, 2024 (26 pp.).
Office Action from corresponding Japanese Patent Application No. 2021-561627 dated Dec. 18, 2023 (18 pp.).
Search Report from corresponding Chinese Patent Application No. 202080040492.0 dated Dec. 1, 2023 (15 pp.).
Office Action from corresponding Israeli Patent Application No. 287281 dated Jun. 9, 2024 (4 pp.).
Decision of Rejection and Decision of Dismissal of Amendment in JP Patent Application No. 2021561627, dated Nov. 5, 2024, with English translations. 12 Pages.
Examination Report dated Dec. 19, 2024 for AU Application No. 2020260148 (3 pp.).
Second Office Action in corresponding Chinese Patent Application No. 202080040492.0, dated Mar. 27, 2025 (14 pp.).
Notification of Provisional Rejection issued in corresponding Korean Patent Application No. 10-2021-7035635 dated Apr. 29, 2025, (22 pp.).

* cited by examiner

VARIABLE-STIFFNESS DISTAL EXTENSION FOR A BLOOD PUMP SYSTEM

CROSS-REFERENCE TO RELATED APPLICATION

This application claims the benefit of the filing date of U.S. Provisional Patent Application No. 62/835,636 filed Apr. 18, 2019, the disclosure of which is hereby incorporated herein by reference.

BACKGROUND OF THE INVENTION

Blood pump assemblies, such as intracardiac or intravascular blood pumps may be introduced in the heart to deliver blood from the heart into an artery. Such mechanical circulatory support devices are often introduced to support the function of the heart after a patient suffers a cardiac episode. One such class of devices is the set of devices known as the "Impella" heart pump. Some blood pump assemblies may be introduced percutaneously through the vascular system during a cardiac procedure. Specifically, blood pump assemblies can be inserted via a catheterization procedure through the femoral artery or the axillary/subclavian artery, into the ascending aorta, across the valve and into the left ventricle. The inserted blood pump assembly may be configured to pull blood from the left ventricle of the heart through a cannula and expels the blood into the aorta. A blood pump assembly may also be configured to pull blood from the inferior vena cava and to expel blood into the pulmonary artery. Some mechanical circulatory support devices are powered by an on-board motor, while others are powered by an external motor and a drive cable.

SUMMARY OF THE INVENTION

The inventors have appreciated that the stability of a blood pump assembly in the ventricle may impact the use and the performance of the pump. For example, positioning a blood pump assembly too close to the ventricle apex can lead to suction of heart tissue into the pump and to arrhythmia problems, and positioning a blood pump assembly too deep in the ventricle can result in the outlet being in the aortic valve or in the ventricle. Further, operation of a blood pump within the heart or movement of the heart muscle itself can create a flow field that displaces the pump in situ. When a blood pump is displaced from the selected operating position, repositioning of the pump is needed, and such repositioning generally requires that the pump be turned off. Such repositioning consumes valuable time and generally interrupts patient care. In some instances, the frequent repositioning of a heart pump within a patient may damage one or both of the pump and the heart. Reducing potential damage to the patient's heart and vasculature while maintaining and improving pump and flow stability is therefore highly desirable. Distal extensions, and in particular atraumatic extensions such as pigtails, may advantageously stabilize the pump within the heart while reducing or minimizing occurrences of trauma to the vasculature or the heart.

In some instances, to avoid or minimize trauma to the heart while effectively stabilizing the blood pump system, it is desirable to have a blood pump system with a distal extension having a stiffness that is lower in a distal portion than a stiffness in a proximal portion. Whereas a stiffer proximal portion reduces buckling and may provide for a desired standoff distance between a pump component (e.g., a pump inlet or outlet) and heart tissue, a less stiff distal portion may aid in avoiding damage to the heart tissue. Some pumps employ a distal extension comprising two sections, each with a different stiffness characteristic, with the distal section having a lower stiffness characteristic than the stiffness characteristic of the proximal section. Such pumps are disclosed for example in U.S. Pat. No. 9,814,814, and generally exhibit a step-wise stiffness profile, with each section of the distal extension having its own stiffness. The step-wise change is stiffness is therefore abrupt. The mechanical properties of such distal extensions are therefore constrained by the number of sections chosen and the materials used for these sections.

The inventors have recognized and appreciated numerous advantages associated with a distal extension for a heart pump system or other medical device that exhibits a continuous stiffness profile. A continuous stiffness profile as used herein lacks abrupt stepwise changes but rather an approximately constant incremental change in stiffness over at least some portion of the length of the distal extension. The resulting profile is more like a slope and less like a step. The slope of the stiffness profile can be in any functional form, i.e. constant, variable, etc. over some portion of the length of the distal extension. As such, the stiffness profiles can be linear, non-linear, etc. For example, a distal extension with a continuous stiffness profile may be better suited for a larger range of anatomical dimensions than a distal extension having a step stiffness profile. Moreover, the distal extensions described herein facilitate retrograde crossing of the aortic valve without the need for a guidewire, for example, to reposition a pump that that inadvertently migrated out of the ventricle and/or to facilitate fully "wireless access" (i.e., access without the need of a guidewire) of the pump into the ventricle. In some instances, such wireless access may be accomplished via continuous deflection of the distal extension as it is advanced against the aortic valve. In particular, instead of becoming trapped in a cusp of the aortic valve, continued advancement of the distal extension may cause the distal extension to deflect and form a loop-like structure, which may subsequently prolapse across the valve and into the left ventricle.

According to some aspects, the systems, methods, and devices described herein provide variable-stiffness distal extensions for a blood pump system or other suitable medical device. In general, a variable-stiffness distal extension has at least one section of continuously varying stiffness, creating a continuous stiffness profile that decreases over at least a portion of the distal extension along the distal direction. The continuously varying stiffness may be implemented by continuously varying at least one radial dimension of the distal extension. For example, in one implementation, the radial dimension that is varied may be an outer diameter of the distal extension, while an inner diameter of the distal extension, defining an interior lumen, is held constant. In this implementation, the thickness of a wall defined by the inner and outer diameters varies with the outer diameter. In one exemplary implementation, the outer diameter of the distal extension decreases along the distal direction while the inner diameter is held constant. In such an implementation, the thickness of the wall decreases along the distal direction. A continuous stiffness profile can be selected by adjusting the outer diameter of the distal extension, with a lower stiffness generally corresponding to a smaller outer diameter. For example, in the above-described implementation, a proximal portion of the distal extension having a larger wall thickness may exhibit a higher stiffness, and the stiffness may decrease continuously in at least a portion of the distal extension along the distal direction as the wall thickness decreases.

According to a first embodiment of the disclosure, a variable-stiffness distal extension for a blood pump system comprises an integrally formed body. The integrally formed body further comprises a distal end and a proximal end. An exterior wall extends between the distal end and the proximal end. An interior wall extends between the distal end and the proximal end. The interior wall forms an interior lumen. The interior lumen is configured to receive a guidewire and can be configured to also receive other longitudinally extending elements. For example, an additional element that the interior lumen may be configured to receive is a guidewire loading aide that can be preassembled in the inner lumen. In another example, an additional element may be a stylet. The interior lumen has a constant diameter between the distal end and the proximal end. The integrally formed body further comprises a proximal portion. The proximal portion of the integrally formed body is configured to be connected to the blood pump system. The proximal portion has a first inner diameter along the interior wall, and a first outer diameter along the exterior wall. The proximal portion further comprises a distal tip portion. The distal tip portion of the proximal portion has a second inner diameter along the interior wall, and a second outer diameter along the exterior wall. The first outer diameter defined by the exterior wall of the distal extension decreases continuously along the proximal portion in the distal direction towards the second outer diameter.

The first outer diameter and the second outer diameter may be selected to yield a specific stiffness profile. In some implementations, the first outer diameter at the proximal end of the distal extension is between about 1 millimeter and about 7.5 millimeters. In such implementations, the second outer diameter at the distal end of the distal extension is between about 0.5 millimeters and about 5 millimeters. In other implementations, the first outer diameter at the proximal end of the distal extension is between about 2.5 millimeters and about 5 millimeters. In such implementations, the second outer diameter at the distal end of the distal extension is between about 3 millimeters and about 4 millimeters. In certain implementations, the first outer diameter at the proximal end of the distal extension is between about 3 millimeters and about 4.5 millimeters. In such implementations, the second outer diameter at the distal end of the distal extension is between about 3.5 millimeters and about 4 millimeters. In further implementations, the first outer diameter at the proximal end of the distal extension is about 4 millimeters. In such implementations, the second outer diameter at the distal end of the distal extension is about 3.75 millimeters. Any of the above ranges for the first outer diameter at the proximal end of the distal extension may be combined with any of the above ranges for the second outer diameter at the distal end of the distal extension to yield the desired variation in diameter along the length of the distal extension, and hence, to yield the desired thickness and stiffness profiles for the distal extension. For example, when the first outer diameter is 9 millimeters at the proximal end, second outer diameter may be 4 millimeters at the distal end. Additionally, when the first outer diameter is 1 millimeter at the proximal end, the second outer diameter may be 0.6 millimeters at the distal end.

At least one advantage of tapering the first outer diameter of the proximal portion in the distal direction is that a section of the proximal portion having a larger outer diameter will be stiffer than a section having a smaller outer diameter. Thus, the stiffness of such an embodiment decreases in the distal direction. A reduced stiffness in the distal direction is desirable for many reasons, at least one of which is that a softer distal end may aid in avoiding the variable-stiffness distal extension causing damage to the vasculature as the extension traverses the vasculature. Similarly, a reduced stiffness distal end may aid in avoiding the distal extension causing damage to the heart valves and/or heart chambers (e.g., ventricle wall tissue) of a patient when the extension is introduced into and positioned within the heart of a patient.

Moreover, according to some aspects, a stiffer proximal portion of a distal extension may aid in stabilizing the pump within the ventricle by allowing the proximal-most portion of the distal extension to maintain its length when thrust forces created by the operation of the pump cause the distal-most portion of the distal extension to bend and/or buckle. For example, the stiffer proximal portion may define a desired "stand-off" distance to maintain a desired spacing between a pump component (e.g., a pump inlet) and the ventricle wall or other tissue in the heart.

In some implementations, a variable-stiffness distal extension may further comprise a second axial portion distal of the first axial portion. In further implementations, the variable-stiffness distal extension may further comprise at least a third axial portion distal of the first axial portion and the second axial portion. Whereas an extension having only two axial portions may comprise a stiffness profile that is piecewise, an integrally formed extension having a decreasing diameter in the distal direction may have a relatively continuous, smooth stiffness profile.

The particular shape of the distal tip portion can be selected to achieve a desired stability of the pump within the heart. The distal tip may generally comprise any curved shape. In some implementations, the variable-stiffness distal extension may have a distal tip portion that is j-shaped. In some implementations, the j-shaped distal tip portion has a radius of curvature between about 5 millimeters and about 15 millimeters. In other implementations, the j-shaped distal tip portion has a radius of curvature between about 7.5 millimeters and about 12.5 millimeters. In certain implementations, the j-shaped distal tip portion has a radius of curvature of about 10 millimeters. In further implementations, the variable-stiffness distal extension may have a distal tip portion that is pigtail-shaped. In certain implementations, the radius of curvature of the pigtail-shaped distal tip portion is constant. In some implementations, the pigtail-shaped distal tip portion has a radius of curvature of between about 5 millimeters and about 15 millimeters. In other implementations, the pigtail-shaped distal tip portion has a radius of curvature between about 7.5 millimeters and about 12.5 millimeters. In certain implementations, the pigtail-shaped distal tip portion has a radius of curvature of about 10 millimeters. In some implementations, the radius of curvature of the pigtail-shaped distal extension decreases in the distal direction. In some implementations, the radius of curvature at the distal end of the distal tip portion is between about 10 percent and about 50 percent less than the radius of curvature at the proximal end of the distal tip portion. In other implementations, the radius of curvature at the distal end of the distal tip portion is between about 20 percent and about 40 percent less than the radius of curvature at the proximal end of the distal tip portion. In certain implementations, the radius of curvature at the distal end of the distal tip portion is about 30 percent less than the radius of curvature at the proximal end of the distal tip portion. In other implementations, the radius of curvature at a point along the distal extension is inversely proportional to the distance of that point along the distal extension from an origin, such that the distal extension assumes the shape of a Euler spiral. At least one advantage of having a j-shaped or a pigtail shaped distal tip portion is that such geometries may help to stabilize the pump within a patient's ventricle.

In certain implementations, the variable-stiffness distal extension may further comprise a lumen. In such implementations, the lumen extends through the entire length of the distal extension. The lumen also may define an inner diameter of the distal extension. The lumen may be configured in its size and its shape to accommodate a guidewire or an additional element other than a guidewire. For example, the additional element may be a guidewire loading aide (e.g., a guidewire loading lumen) or a stylet. In some implementations, the inner diameter of the distal extension (which may be defined by the lumen) is constant throughout the length of the distal extension. In some implementations, the inner diameter defined by the lumen may be between about 0.1 millimeters and about 5.5 millimeters. In further implementations, the inner diameter may be between about 1 millimeter and 3 millimeters. At least one advantage of the incorporation of a lumen having a constant inner diameter is that it can yield a desired continuous stiffness profile when coupled with a distal extension of continuously varying outer diameter. Additionally, an inner lumen is generally useful as it allows the introduction of a guidewire while maintaining a small insertion profile and allowing the device to maintain a continuous stiffness profile. In other implementations, the inner diameter of the distal extension defined by the lumen continuously decreases between the proximal end of the first axial portion and the distal end of the first axial portion. In some implementations, the inner diameter of the distal extension decreases from about 5.5 millimeters at the proximal end of the first axial portion to about 0.1 millimeters at the distal end of the first axial portion. In other implementations, the inner diameter of the distal extension decreases from about 3 millimeters at the proximal end of the first axial portion to about 1 millimeter at the distal end of the first axial portion. At least one advantage of a lumen with an inner diameter that decreases between the proximal end of the first axial portion and the distal end of the first axial portion is that a desired continuous stiffness profile can be attained by the combining the decreasing inner diameter with a decreasing outer diameter.

In another embodiment, a variable-stiffness distal extension for a blood pump system comprises a flexible elongate body. The flexible elongate body of the distal extension has a distal end and a proximal end. The flexible elongate body may further comprise an exterior wall. The exterior wall is configured to extend between the distal and proximal ends of the distal extension. The flexible elongate body is further configured with a first axial portion, a second axial portion, and a distal tip portion. The second axial portion is distal of the first axial portion and is integrally formed with the first axial portion. The distal tip portion is positioned distally relative to the second axial portion. The distal tip portion is further integrally formed with the second axial portion. An outer diameter of the exterior wall of the flexible elongate body is configured to decrease continuously from the proximal end of the distal extension to the distal end of the distal extension. At least one advantage of the continuously decreasing outer diameter of the exterior wall is that sections along the length of the distal extension with larger outer diameters have increased stiffness, and sections with smaller outer diameters have decreased stiffness, such that the continuous stiffness profile of a distal extension with an outer diameter decreasing in the distal direction also decreases in the distal direction. As discussed previously, a continuous stiffness profile that decreases in the distal direction may provide numerous benefits. For example, a soft distal end may allow the practitioner to easily introduce the distal extension into a patient's vasculature without damaging the vasculature. Moreover, the relatively stiff proximal end of the distal extension, corresponding to the section with a larger outer diameter may aid in stabilizing the pump within the ventricle by allowing the proximal-most portion of the distal extension to maintain its length (e.g., by defining a desired "stand-off" distance) when thrust forces created by the operation of the pump cause the distal-most portion of the distal extension to bend and/or buckle. Similarly, the relatively stiff proximal end of the distal extension, corresponding to the section with a larger outer diameter, may help to stabilize the pump within the heart valve and the heart chambers of the patient.

In some implementations, the outer diameter of the distal extension continuously decreases from about 6 millimeters at the proximal end of the first axial portion to about 0.5 millimeters at the distal end of the first axial portion. In other implementations, the outer diameter of the distal extension continuously decreases from about 4 millimeters at the proximal end of the first axial portion to about 2 millimeters at the distal end of the first axial portion. In certain implementations, the outer diameter of the distal extension is constant between a proximal end of the second axial portion and a distal end of the second axial portion. In some implementations, the first axial portion has a first stiffness. Further, the second axial portion has a second stiffness. In some implementations, the first stiffness is greater than the second stiffness. As discussed previously, a practitioner will be able to manipulate the extension through the vasculature of a patient, due to its stiff proximal end, while the soft distal end will allow the extension to be advanced through the vasculature without damaging the vasculature.

In certain implementations, the distal extension further comprises a third pigtail-shaped portion. The third pigtail-shaped portion has a third stiffness. This third stiffness is less than the second stiffness. In some implementations, the first axial portion has a first axis. The second axial portion has a second axis. In certain implementations, the first axis is not parallel to the second axis. In some implementations, the first axis and the second axis are oriented at an angle relative to each other. In some implementations, this angle ranges from about 0 degrees to about 50 degrees. In other implementations, the angle ranges from about 10 degrees to about 40 degrees. In yet other implementations, the angle between the first axis and the second axis is ranges from between about 15 degrees to about 35 degrees. In certain implementations, the angle between the first axis and the second axis is about 30 degrees. The particular angle at which the first axis and the second axis are oriented can be selected to yield certain structural properties of the distal extension. For example, the angle can be selected to increase the ease with which a practitioner maneuvers the extension through the patient's vasculature. The angle can also be adjusted to maximize the ease with which the pump and the extension cross the aortic valve. Additionally, the angle may be selected to provide the most stable configuration of the blood pump system within the ventricle.

In some implementations, the distal extension may be integrally formed from one or more materials. For example, a distal extension may be formed from a single material with varying dimensions along the length of the distal extension to provide the desired mechanical properties. Alternatively or additionally, the material of the distal extension may be varied along a length of the distal extension. For example, a distal extension may be formed as a composite structure comprising two or more materials, and a configuration of the two or more materials may be varied along the length of the distal extension. In another example, a material of a distal tip section can be selected to have a smaller stiffness than a material of a proximal section. In view of the above, it should be appreciated that by varying the materials and/or dimension of the distal extension, a desired mechanical response may be achieved, such as a stiffness profile that varies along the length of the distal extension.

Generally, the material(s) of the distal extension may be selected such that the distal extension has a sufficiently smooth surface so as to avoid or prevent biologic contamination, fouling, and/or adhesion of the distal extension. In this manner, the material of the distal extension may aid in reducing or preventing thrombus formation. In certain implementations, the distal extension comprises polyurethane. In other implementations, the distal extension comprises a polyamide. The polyamide may comprise PEBAX® or nylon. PEBAX is an elastomer that is a block copolymer having rigid polyamide blocks and soft polyether blocks. In further implementations, the distal extension may comprise an elastomeric polymer, or an elastomer. The elastomer may comprise one or more silicone-based polyurethanes or one or more polycarbonate-based polyurethanes. One such polycarbonate-based polyurethane elastomeric polymer is 55D Pellethane®. In another implementation, the elastomer comprises a blend of these silicone or polycarbonate-based polyurethanes and other elastomers or a compound of these silicone or polycarbonate-based polyurethanes and other elastomers. The elastomer blends and compounds may contain different ratios of such polymers. In other implementations, the distal extension may comprise a blend or a compound of the above elastomers in addition to additives, fillers, and colorants. For example, the use of additives, fillers, and colorants may be used to enhance any combination of the fluoroscopic visualization, the echographic visualization, and the stiffness modulation of the distal extension. Moreover, it should be appreciated that the distal extensions described herein may be formed in any suitable manner. For example, a distal extension may be formed by a suitable molding and/or extrusion process.

In further implementations, the outer diameter of the distal extension decreases continuously in the distal direction in a third portion of the distal extension. In some implementations, the outer diameter of the distal extension decreases continuously over the entire length of the third portion. In other implementations, the outer diameter of the distal extension decreases continuously over about the first 10 percent and about 60 percent of the length of the third portion. In certain implementations, the outer diameter of the distal extension decreases continuously over about the first 20 percent and about 50 percent of the length of the third portion. In other implementations, the outer diameter of the distal extension decreases continuously over about the first 30 percent and about 40 percent of the length of the third portion. In some implementations, the outer diameter of the distal extension decreases continuously over about the first 35 percent of the length of the third portion. In some implementations, the outer diameter of the distal extension decreases in the third portion to between about 55 percent and about 95 percent of the outer diameter of the distal extension in the first portion. In other implementations, the outer diameter of the distal extension decreases in the third portion to between about 65 percent and about 85 percent of the outer diameter of the distal extension in the first portion. In certain implementations, the outer diameter of the distal extension decreases in the third portion to between about 75 percent of the outer diameter of the distal extension in the first portion. In other implementations, the second portion comprises a material having a first flexural modulus, and the third portion comprises a material having a second flexural modulus. In some implementations, the first flexural modulus is greater than the second flexural modulus. For example, the first flexural modulus may be greater than the second flexural modulus by between a factor of about 1 and a factor of about 5. In another example, the first flexural modulus may be greater than the second flexural modulus by between a factor of about 1.5 and a factor of about 3.5. In one example, the first flexural modulus may be greater than the second flexural modulus by a factor of about 2. The exact ratio of the flexural moduli of the material of the second portion to the material of the third portion can be selected to provide a relatively smooth stiffness profile along the length of the distal extension and preventing a transition point between the second portion and the third portion from becoming a locus for kinking.

In certain implementations, the first axial portion, the second axial portion, and the third distal tip portion are each sized and shaped such that the first axial portion is stiffer than the second axial portion, and such that the second axial portion is stiffer than the third distal tip portion. In other implementations, the third distal tip portion is configured to have a lower stiffness than the second axial portion. In other implementations, the outer diameter of the distal extension decreases in the third distal tip portion. In certain implementations, the outer diameter of the distal extension decreases between a proximal end and a distal end of the third distal tip portion. In certain implementations, the inner diameter of the third portion of the distal extension is constant along the third portion.

In another embodiment, a blood pump system comprises a distal flexible extension. The blood pump system comprises a catheter and a blood pump. The blood pump has a distal end and a proximal end. The system further comprises a cannula, the cannula being coupled to the distal end of the blood pump, and a cage positioned distal the cannula. A variable stiffness distal extension is attached to the cage. The variable stiffness distal extension may be any of the extensions described in the application.

In some implementations, the blood pump system is configured to be inserted through the vasculature of a patient without a guidewire. In such implementations, the distal extension may comprise a partial lumen, or the distal extension may be solid throughout its length. In other implementations, the blood pump system is configured to be inserted through the vasculature of a patent using a guidewire. In such implementations, the distal extension may comprise an interior lumen through its entire length. In certain implementations, the variable stiffness distal tip is configured to create a stiffness gradient between the proximal end of the variable stiffness distal tip and a location distal of the proximal end of the variable stiffness distal tip. In other implementations, the variable stiffness distal tip of the blood pump system is configured to cross the aortic valve.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, method, and devices disclosed herein, certain illustrative embodiments will be described. Although the embodiments and features described herein are specifically described for use in connection with a pump for a heart, it will be understood that the teachings may be adapted and applied to other pumps and other types of medical devices.

The systems, method, and devices described herein provide an integrally formed variable-stiffness distal extension for a blood pump system. In general, the system comprises an extension having a proximal portion and a distal tip portion. In such implementations, the proximal portion may have an outer diameter that is greater than an outer diameter of the distal tip portion. The outer diameter of the proximal portion of the distal extension is generally configured to decrease in the distal direction. This gradual reduction in outer diameter along the length of the distal extension creates a continuous stiffness profile along the length of the distal extension that decreases in the distal direction. The relatively soft distal end of the distal extension created by such a continuous stiffness profile allows the extension to be introduced into the vasculature of a patient without damaging the vasculature as the extension contacts the walls of the patient's blood vessels, and in some instances, may aid in facilitating crossing of the aortic valve without the use of a guidewire, ads discussed previously. Simultaneously, the relatively stiff proximal end of the distal extension created by such a continuous stiffness profile allows the extension to be easily maneuverable through the vasculature by a practitioner, and may aid in defining a desired "stand-off" distance when the pump is positioned in a ventricle, as discussed previously. The outer diameter can be adjusted along the length of the distal extension to establish and maintain a desired continuous stiffness profile along the length of the distal extension.

Figure 1:
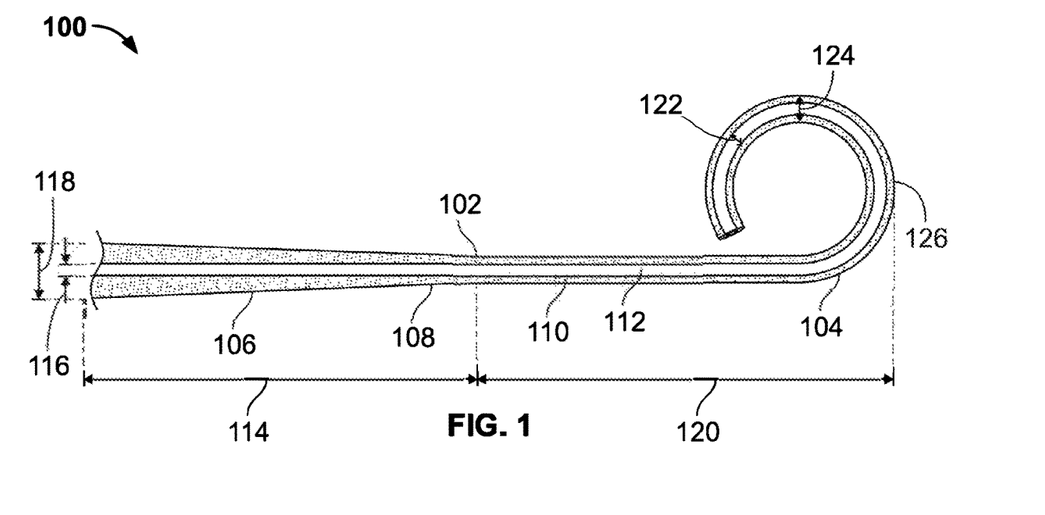
FIG. 1 shows an illustrative example of an integrally formed variable-stiffness distal extension comprising an interior lumen.

FIG. 1 shows an illustrative example of an integrally formed variable-stiffness distal extension 100 for a blood pump system comprising an interior lumen. Distal extension 100 further comprises body 102, distal end 104, proximal end 106, exterior wall 108, interior wall 110, interior lumen 112, proximal portion 114, first inner diameter 116, first outer diameter 118, distal tip portion 120, second inner diameter 122, second outer diameter 124, and distal tip 126. Proximal end 106 of body 102 of distal extension 100 is configured to be attached to a blood pump system. Exterior wall 108 of distal extension 100 defines at least a first outer diameter 118 and a second outer diameter 124. First outer diameter 118 at the proximal end 106 of body 102 decreases continuously in the distal direction towards second outer diameter 124 at distal end 104 of body 102. Distal tip 126 is extends from the distal end of distal tip portion 120. As described below in relation to FIG. 6, in some implementations, distal tip 126 is configured to be in a pigtail shape. As described below in relation to FIG. 7, in other implementations, distal tip 126 is configured to be in a "j" shape. Distal tip 126 may further comprise any other curved shape. Distal tip 126 may aid in stabilizing the pump within the ventricle and may aid in avoiding suction of heart tissue into the pump during operation.

In some implementations, first outer diameter 118 at the proximal end 106 of the distal extension 100 is between about 1 millimeter and about 7.5 millimeters. In such implementations, second outer diameter 124 at the distal end 104 of the distal extension 100 is between about 0.5 millimeters and about 5 millimeters. In other implementations, first outer diameter 118 at the proximal end 106 of the distal extension 100 is between about 2.5 millimeters and about 5 millimeters. In such implementations, second outer diameter 124 at the distal end 104 of the distal extension 100 is between about 3 millimeters and about 4 millimeters. In certain implementations, first outer diameter 118 at the proximal end 106 of the distal extension 100 is between about 4 millimeters and about 6 millimeters. In such implementations, second outer diameter 124 at the distal end 104 of the distal extension 100 is between about 3 millimeters and about 4 millimeters. In further implementations, first outer diameter 118 at the proximal end 106 of the distal extension 100 is about 4 millimeters. In such implementations, second outer diameter 124 at the distal end 104 of the distal extension 100 is about 3.75 millimeters. At least one advantage of the decrease in first outer diameter 118 to second outer diameter 124 in the distal direction is that the proximal portion 114 of body 102 having a larger diameter will be stiffer than distal portion 120 of body 102 having a smaller diameter. As such, the stiffness of such an implementation decreases in the distal direction. As discussed previously, such arrangements having a continuously variable stiffness profile may allow a practitioner to guide the extension through the vasculature of a patient more easily, and will be able to do so without damaging the vasculature of the patient. Interior wall 110 defines interior lumen 112, first inner diameter 116, and second inner diameter 122. In some implementations, including the illustrative example shown in FIG. 1, first inner diameter 116 and second inner diameter 122 are equivalent, which is to say that the inner diameter throughout the entire length of body 102 is constant.

Alternatively, first inner diameter 116 can also be greater than second inner diameter 122, corresponding to a decrease in first inner diameter 116 in the distal direction along the length of body 102. In some implementations, first inner diameter 116 defined by interior lumen 112 may be between about 0.1 millimeters and about 5.5 millimeters. In further implementations, first inner diameter 116 may be between about 1 millimeter and 3 millimeters. In some implementations, second inner diameter 122 defined by interior lumen 212 may be between about 0.5 millimeters and about 5.5 millimeters. In further implementations, second inner diameter 122 may be about 2 millimeters.

Figure 2:
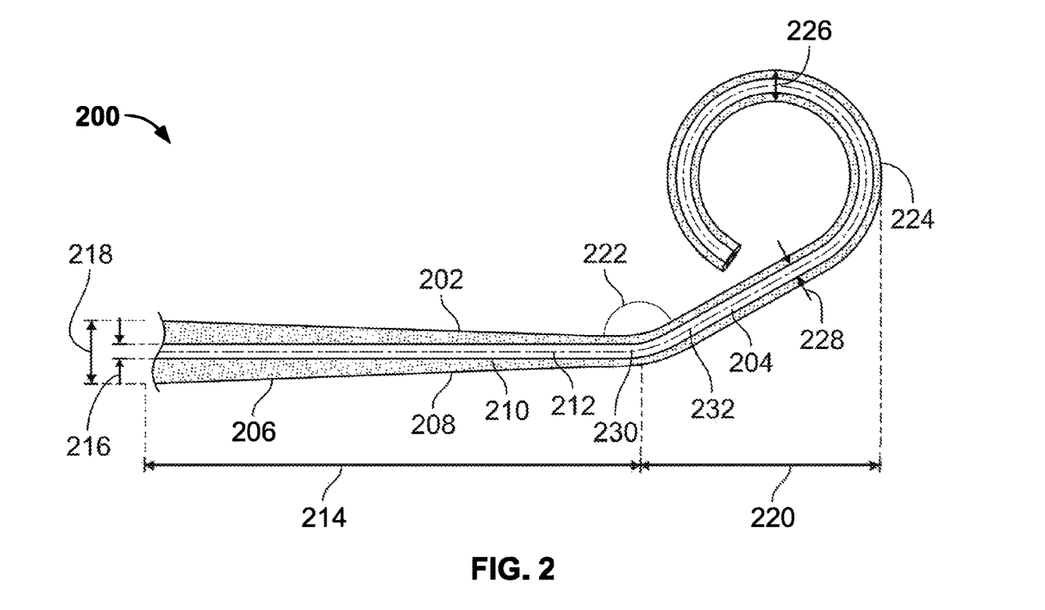
FIG. 2 shows an illustrative example of an integrally formed variable-stiffness distal extension comprising first and second axial portions.

FIG. 2 shows another illustrative example of an integrally formed variable-stiffness distal extension 200 for a blood pump system having a first axial portion 214 and a second axial portion 220 offset relative to each other by angle 222. Distal extension 200 further comprises body 202, distal end 204, proximal end 206, exterior wall 208, interior wall 210, interior lumen 212, first axial portion 214, first inner diameter 216, first outer diameter 218, second axial portion 220, angle 222, distal tip 224, second outer diameter 226, second inner diameter 228, first axis 230, and second axis 232. Proximal end 206 of body 202 of distal extension 200 is configured to be attached to a blood pump system. Exterior wall 208 of distal extension 200 defines first outer diameter 218 and second outer diameter 226. First outer diameter 218 at the proximal end 206 of body 202 may decrease continuously in the distal direction towards second outer diameter 226 at distal end 204 of body 202.

As previously discussed, the variable-stiffness distal extension may further comprise at least a third axial portion distal of first axial portion 214 and second axial portion 220. Whereas an extension having only two axial portions may comprise a stiffness profile that is piecewise, an integrally formed extension having a decreasing diameter in the distal direction may have a relatively continuous, smooth stiffness profile. In some implementations, first axial portion 214 comprises a first material, second axial portion 220 comprises a second material, and the third axial portion comprises a third material. For example, second axial portion 220 may comprise a material having a first flexural modulus, and the third portion may comprise a material having a second flexural modulus. In some implementations, the first flexural modulus is greater than the second flexural modulus. For example, the first flexural modulus may be greater than the second flexural modulus by between a factor of about 1 and a factor of about 5. In another example, the first flexural modulus may be greater than the second flexural modulus by between a factor of about 1.5 and a factor of about 3.5. In one example, the first flexural modulus may be greater than the second flexural modulus by a factor of about 2. The exact ratio of the flexural moduli of the material of the second portion to the material of the third portion can be selected to provide a relatively smooth stiffness profile along the length of the distal extension and avoiding a distinct transition point between the second portion and the third portion from becoming a locus for kinking and/or bending.

As previously discussed, at least one advantage of the decrease in first outer diameter 218 to second outer diameter 226 in the distal direction is that the stiffness of such an implementation decreases in the distal direction. Accordingly, a practitioner may be able to guide the extension having such a continuously variable lengthwise stiffness profile through the vasculature of a patient more easily, and may be able to do so without damaging the vasculature of the patient. Interior wall 210 defines interior lumen 212, first inner diameter 216, and second inner diameter 228. In some implementations, including the illustrative example shown in FIG. 2, first inner diameter 216 and second inner diameter 228 are equivalent, which is to say that the inner diameter throughout the entire length of body 202 is constant. In some implementations, first inner diameter 216 is greater than second inner diameter 228, corresponding to a decrease in first inner diameter 216 in the distal direction along the length of body 202. First axial portion 214 defines first axis 230. Second axial portion 220 defined second axis 232. First axis 230 and second axis 232 are offset relative to one another by angle 222. In some implementations, first axis 230 and second axis 232 are oriented at angle 222 between about 0 degrees to about 50 degrees with respect to each other. In other implementations, angle 222 ranges from about 10 degrees to about 40 degrees. In yet other implementations, angle 222 between first axis 330 and second axis 232 is ranges from between about 15 degrees to about 35 degrees. In certain implementations, angle 222 between first axis 230 and second axis 232 is about 30 degrees. At least one advantage of having first axial portion 214 offset from second axial portion 220 by angle 222 is that angle 222 may allow the practitioner to maneuver the pump more easily through the patient's vasculature and across the aortic valve.

Figure 3:
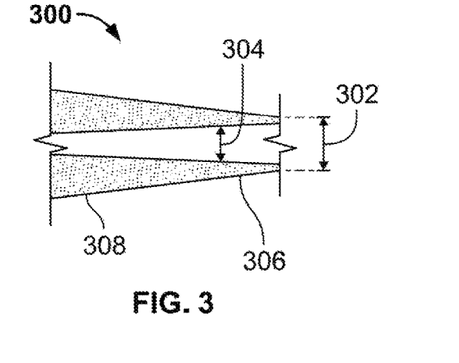
FIG. 3 shows an illustrative example of an integrally formed distal extension comprising a variable outer diameter and a variable inner diameter.

FIG. 3 shows an illustrative profile 300 of an integrally formed variable-stiffness distal extension having variable outer diameter 302, variable inner diameter 304, distal end 306, and proximal end 308. Outer diameter 302 is configured to decrease from proximal end 308 to distal end 306. Inner diameter 304 is configured to increase from proximal end 308 to distal end 306. In such an implementation, the stiffness of the distal extension decreases in the distal direction. One advantage of such a configuration is that the rate of decrease of outer diameter 302 and the rate of increase of inner diameter 304 can be selected to fine-tune the continuous stiffness profile along the length of the distal extension.

Figure 4:
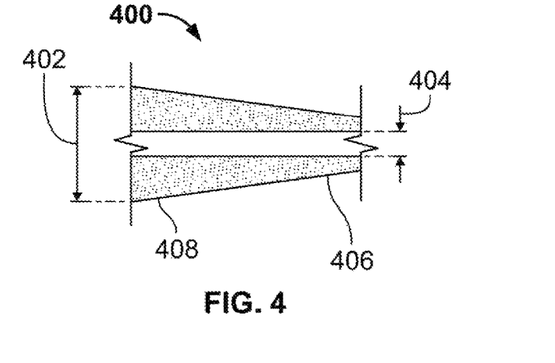
FIG. 4 shows an illustrative example of an integrally formed distal extension comprising a variable outer diameter and a constant inner diameter.

FIG. 4 shows an illustrative profile 400 having variable outer diameter 402, constant inner diameter 404, distal end 406, and proximal end 408. Outer diameter 402 is configured to decrease towards distal end 406 from proximal end 408. This configuration lends to the distal extension a continuous stiffness profile that decreases in the distal direction. Such a continuous stiffness profile may allow the extension to be easily maneuverable through the vasculature of a patient, while also avoiding the extension from damaging the vasculature as it is introduced into the patient.

Figure 5A:
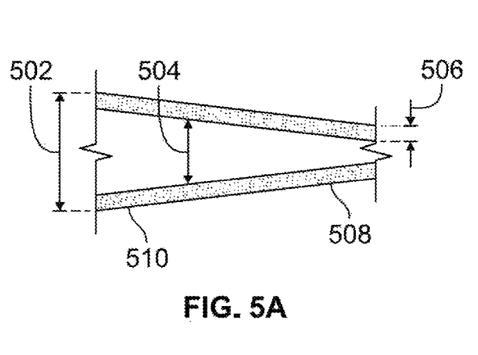
FIGS. 5A-5C show three illustrative examples of integrally formed distal extensions comprising a variable inner diameter and a variable outer diameter.
Figure 5B:
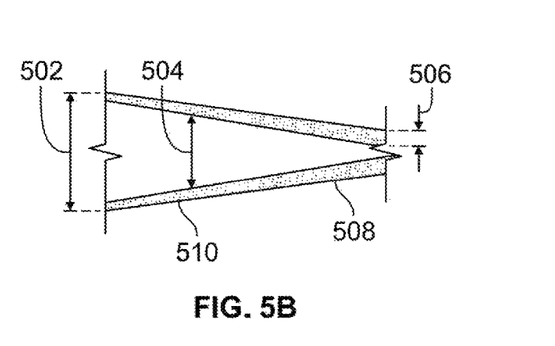
Figure 5C:
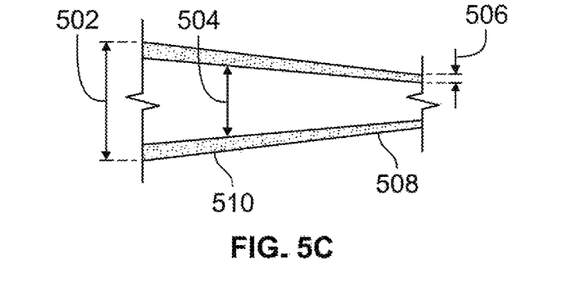

FIG. 5 shows an illustrative profile of an integrally formed variable-stiffness distal extension having variable outer diameter 502, variable inner diameter 504, thickness 506, distal end 508, and proximal end 510. Variable outer diameter 502 and variable inner diameter 504 are both configured to decrease from proximal end 510 in the direction of distal end 508. FIGS. 5A, 5B, and 5C depict illustrative examples of the rates of decrease of the outer diameter 502 and the inner diameter 504. The relative rates of decrease of outer diameter 502 and inner diameter 504 control the variability of thickness 506. In FIG. 5A, outer diameter 502 and outer diameter 504 decrease at the same rate such that thickness 506 is constant. In some implementations, outer diameter 502 and outer diameter 504 may decrease at different rates such that thickness 506 is variable as well. FIG. 5B shows inner diameter 504 decreasing at a greater rate than outer diameter 502. As such, thickness 506 increases in the distal direction. FIG. 5C shows outer diameter 502 decreasing at a greater rate than inner diameter 504 such that thickness 506 decreases in the distal direction. The stiffness of the illustrative example shown in FIG. 5C decreases in the distal direction.

Figure 6A:
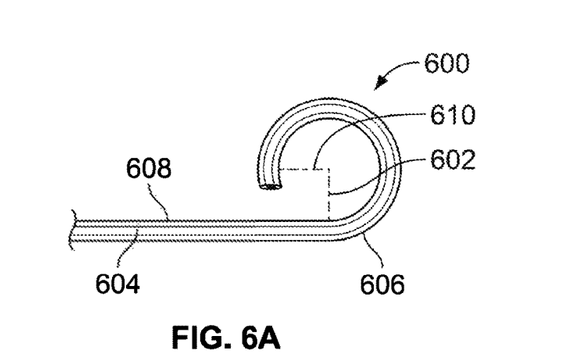
FIG. 6A shows an illustrative example of a pigtail-shaped distal tip having a constant radius of curvature.
Figure 6B:
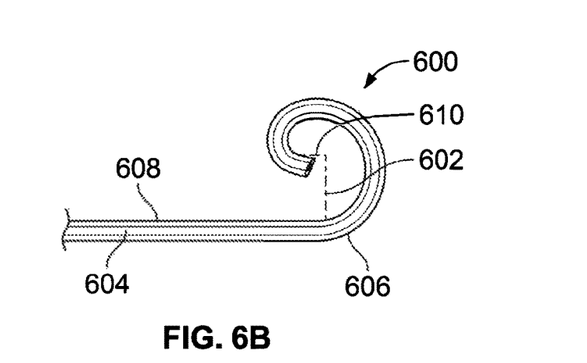
FIG. 6B shows an illustrative example of a pigtail-shaped distal tip having a variable radius of curvature.

FIG. 6A-B show illustrative examples of a pigtail-shaped distal tip 600. FIG. 6A shows pigtail-shaped distal tip 600 having a constant radius of curvature and FIG. 6B shows pigtail-shaped distal tip having a variable radius of curvature. Pigtail-shaped distal tip 600 generally has radius of curvature 602 and 610, lumen 604, distal end 606, and proximal end 608. Lumen 604 extends along the entire length of distal tip 600. Radius of curvature 602 may be configured to be constant or variable along the length of distal tip 600. FIG. 6A shows such a pigtail-shaped distal tip having a constant radii of curvature 602 and 610. FIG. 6B shows a pigtail-shaped distal tip having a decreasing radii of curvature 602 and 610, where 602 is larger than 610. In some implementations, the pigtail-shaped distal tip portion has radius of curvature 602 of between about 5 millimeters and about 15 millimeters. In other implementations, the pigtail-shaped distal tip portion has radius of curvature 602 between about 7.5 millimeters and about 12.5 millimeters. In certain implementations, the pigtail-shaped distal tip portion has radius of curvature 602 of about 10 millimeters. FIG. 6B shows distal tip 600 having variable radii of curvature 602 and 610. Specifically, FIG. 6B shows the illustrative example of distal tip 600 in which radius of curvature 602 decreases from proximal end 608 to distal end 606 to yield radius of curvature 610. In some implementations, radius of curvature 610 at distal end 606 of the distal tip portion 600 is between about 10 percent and about 50 percent less than radius of curvature 602 at the proximal end 608 of distal tip portion 600. In other implementations, radius of curvature 610 at distal end 606 of distal tip portion 600 is between about 20 percent and about 40 percent less than radius of curvature 602 at proximal end 608 of distal tip portion 600. In certain implementations, radius of curvature 610 at distal end 606 of distal tip portion 600 is about 30 percent less than radius of curvature 602 at proximal end 608 of distal tip portion 600. In other implementations, distal tip 600 forms a portion of a Euler spiral, such that radius of curvature 602 at a point along distal tip portion 600 is inversely proportional to the distance of that point along distal tip portion 600 from an origin.

Figure 7A:
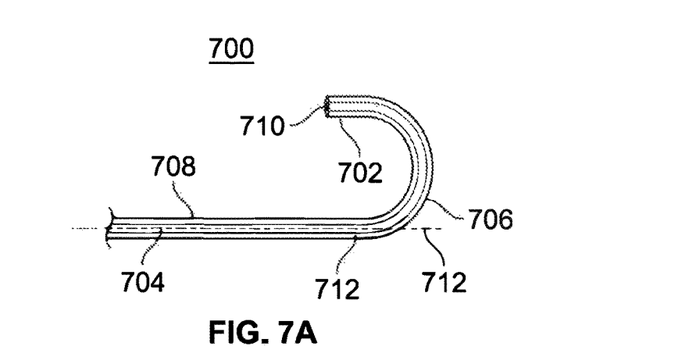
FIG. 7A shows an illustrative example of a j-shaped distal tip portion.
Figure 7B:
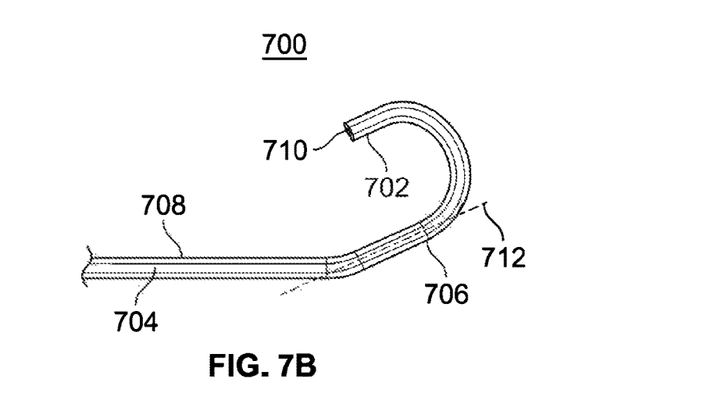
FIG. 7B shows an illustrative example of a distal extension having first and second axial portions and a j-shaped distal tip.

FIGS. 7A-B show illustrative examples of a j-shaped distal tip 700 having radius of curvature 702, lumen 704, distal end 706, proximal end 708, distal-most point 710, and axis 712. FIG. 7A shows such a distal tip 700 having a single axial portion, and FIG. 7B shows such a distal tip 700 having a first axial portion 714 and a second axial portion 716. Lumen 704 extends along the entire length of distal tip 700. J-shaped distal tip 700 may have a constant radius of curvature 702. In some implementations, radius of curvature 702 may decrease along the length of distal tip 700. In other implementations, radius of curvature 702 may increase along the length of distal tip 700. J-shape distal tip 700 is configured such that a line tangent to distal-most point 710 is parallel to axis 712 along the length of the distal extension.

The foregoing is merely illustrative of the principles of the disclosure, and the apparatuses can be practiced by other than the described aspects, which are presented for purposes of illustration and not of limitation. It is to be understood that the apparatuses disclosed herein, while shown for use in pumps, may be applied to other apparatuses, such as other intravascular medical devices. Variations and modifications will occur to those of skill in the art after reviewing this disclosure. The disclosed features may be implemented, in any combination and subcombination (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A variable stiffness distal extension for a blood pump system, the variable stiffness distal extension comprising:
   an integrally formed body comprising:
   a distal end,
   a proximal end configured to be attached to a distal end of a blood pump system,
   an exterior wall extending between the distal and proximal ends,
   an interior wall defining a lumen extending between the proximal end and the distal end, wherein the lumen is constructed and arranged to receive a longitudinally extending element,
   a proximal portion having a distal end and a proximal end and extending along a first axis from the proximal end to the distal end of the proximal portion, and
   a distal portion having a distal end and a proximal end, wherein the proximal end of the distal portion is connected to and abuts the distal end of the proximal portion and the distal portion extends along a second axis distally from the proximal portion,
   wherein the first axis is not parallel to the second axis,
   wherein an outer diameter of the integrally formed body defined by the exterior wall decreases continuously from the proximal end to the distal end of the proximal portion along a distal direction,
   wherein the interior lumen has an inner diameter that decreases continuously along the distal direction from the proximal end to the distal end of the proximal portion,
   wherein, from the proximal end to the distal end of the proximal portion, the outer diameter of the integrally formed body and the inner diameter of the lumen each decrease at different rates along the distal direction, and
   wherein, from the proximal end to the distal end of the distal portion, the outer diameter of the integrally formed body is constant.

2. The variable stiffness distal extension of claim 1, wherein the longitudinally extending element that the lumen is constructed and arranged to receive is at least one of a guidewire, a guidewire loading aide, or a stylet.

3. The variable stiffness distal extension of claim 1, wherein the integrally formed body further comprises a distal tip portion extending from the distal portion and the distal tip portion comprises a curved shape.

4. The variable stiffness distal extension of claim 3, further comprising a pigtail portion wherein a material of the pigtail portion comprises at least one polymer.

5. The variable stiffness distal extension of claim 4, wherein the at least one polymer comprises at least one of polyurethane, a polyamide, and an elastomer.

6. The variable stiffness distal extension of claim 5, wherein the polyamide comprises at least one of PEBAX and nylon.

7. The variable stiffness distal extension of claim 5, wherein the elastomer comprises a thermoplastic polyurethane.

8. The variable stiffness distal extension of claim 4, wherein the material of the pigtail portion further comprises at least one of an additive, a colorant, and a filler.

9. The variable stiffness distal extension of claim 3, wherein the distal tip portion is j-shaped or pigtail-shaped.

10. The variable stiffness distal extension of claim 3, wherein the outer diameter of the integrally formed body is constant from a proximal end to a distal end of the distal tip portion.

11. The variable stiffness distal extension of claim 1, wherein the inner diameter from the proximal end to the distal end of the proximal portion decreases from about 3 millimeters to about 0.1 millimeter.

12. The variable stiffness distal extension of claim 1, wherein the longitudinally extending element that the lumen is configured to receive is a guidewire loading aide.

13. The variable stiffness distal extension of claim 1, wherein the longitudinally extending element that the lumen is configured to receive is a stylet.

14. The variable stiffness distal extension of claim 1, wherein the distal extension is integrally formed of a single material.

15. The variable stiffness distal extension of claim 1, wherein the proximal portion is a first portion, the distal portion is a second portion and further comprising a third portion that is distal to the second portion, wherein the third portion is configured to have a lower stiffness than the second portion.

16. The variable stiffness distal extension of claim 15, wherein a material of the third portion has a lower flexural modulus than a material of the second portion.

17. A variable stiffness distal extension for a blood pump system, the variable stiffness distal extension comprising:
a flexible elongate body having a distal end and a proximal end, and an exterior wall extending between the distal and proximal ends, the proximal end configured to be attached to a distal end of the blood pump system, wherein the body is further configured with a first axial portion, a second axial portion, and a distal tip portion;
wherein the second axial portion is distal of the first axial portion and is integrally formed with the first axial portion,
wherein the first axial portion and the second axial portion each have a proximal end and a distal end and the proximal end of the second axial portion is connected to and abuts the distal end of the first axial portion,
wherein the first axial portion extends along a first axis from the proximal end to the distal end of the first axial portion, the second axial portion extends along a second axis from the proximal end to the distal end of the second axial portion, wherein the second axis is not parallel to the first axis,
wherein the distal tip portion is distal of the second axial portion and is integrally formed with the second axial portion,
wherein an outer diameter of the exterior wall decreases continuously from a the proximal end to the distal end of the first axial portion,
wherein an inner diameter of the distal extension decreases continuously from the proximal end of the first axial portion to the distal end of the first axial portion,
wherein, from the proximal end to the distal end of the first axial portion, the outer diameter of the exterior wall and the inner diameter of the distal extension each decrease at different rates, and
wherein, from the proximal end of the second axial portion to the distal end of the second axial portion, the outer diameter of the exterior wall is constant.

18. The variable stiffness distal extension of claim 17, wherein the variable stiffness distal extension comprises a lumen extending through an entire length of the variable stiffness distal extension, the lumen defining the inner diameter of the distal extension.

19. The variable stiffness distal extension of claim 18, wherein the inner diameter of the distal extension is sized and shaped to accommodate an element through the lumen.

20. The variable stiffness distal extension of claim 17, wherein, from the proximal end of the first axial portion to the distal end of the first axial portion, the inner diameter of the distal extension decreases from about 3 millimeters to about 1 millimeters.

21. The variable stiffness distal extension of claim 17, wherein the outer diameter continuously decreases from 4 millimeters at the proximal end of the first axial portion to 2 millimeters at the distal end of the first axial portion.

22. The variable stiffness distal extension of claim 17, wherein the first axial portion has a first stiffness, the second axial portion has a second stiffness, and the first stiffness is greater than the second stiffness.

23. The variable stiffness distal extension of claim 22, wherein the distal tip portion is a third axial portion.

24. The variable stiffness distal extension of claim 23, wherein the third axial portion is pigtail-shaped.

25. The variable stiffness distal extension of claim 24, wherein the third axial portion has a third stiffness, and the second stiffness is greater than the third stiffness.

26. The variable stiffness distal extension of claim 17, wherein an angle between the first axis and the second axis is between about 1 degree and about 50 degrees.

27. The variable stiffness distal extension of claim 26, wherein the angle between the first axis and the second axis is between about 15 degrees and about 35 degrees.

28. The variable stiffness distal extension of claim 26, wherein the angle between the first axis and the second axis is about 30 degrees.

29. The variable stiffness distal extension of claim 17, wherein the first axial portion, the second axial portion, and the distal tip portion are each sized and shaped such that the first axial portion is stiffer than the second axial portion, and the second axial portion is stiffer than the distal tip portion.

30. The variable stiffness distal extension of claim 29, wherein the distal tip portion is configured to have a lower stiffness than the second axial portion.

31. The variable stiffness distal extension of claim 29, wherein the outer diameter of the distal extension decreases in the distal tip portion.

32. The variable stiffness distal extension of claim 30, wherein the outer diameter of the distal extension decreases between a proximal end and a distal end of the distal tip portion.

* * * * *

UNITED STATES PATENT AND TRADEMARK OFFICE
CERTIFICATE OF CORRECTION

PATENT NO. : 12,383,704 B2
APPLICATION NO. : 16/851920
DATED : August 12, 2025
INVENTOR(S) : Alexander Ship et al.

Page 1 of 1

It is certified that error appears in the above-identified patent and that said Letters Patent is hereby corrected as shown below:

In the Specification

Detailed Description
Column 12, Line 8:
Now reads: "330"; should read -- 230 --

In the Claims

Claim 17
Column 15, Line 48:
Now reads: "from a"; should read -- from --

Claim 20
Column 16, Line 16:
Now reads: "millimeters."; should read -- millimeter. --

Signed and Sealed this
Eighteenth Day of November, 2025

John A. Squires
*Director of the United States Patent and Trademark Office*